(12) United States Patent
Kim et al.

(10) Patent No.: US 9,701,767 B2
(45) Date of Patent: Jul. 11, 2017

(54) SUPER ABSORBENT POLYMER CONTAINING WATER-SOLUBLE SALT AND PREPARATION METHOD THEREFOR

(71) Applicant: LG Chem, Ltd., Seoul (KR)

(72) Inventors: Young-Sam Kim, Daejeon (KR); Yeon-Woo Hong, Daejeon (KR); Hyun-Jin Lee, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/036,291

(22) PCT Filed: Jun. 10, 2015

(86) PCT No.: PCT/KR2015/005844
§ 371 (c)(1),
(2) Date: May 12, 2016

(87) PCT Pub. No.: WO2015/199363
PCT Pub. Date: Dec. 30, 2015

(65) Prior Publication Data
US 2016/0280862 A1 Sep. 29, 2016

(30) Foreign Application Priority Data

Jun. 23, 2014 (KR) .................. 10-2014-0076594
Jun. 9, 2015 (KR) .................. 10-2015-0081378

(51) Int. Cl.
| | | |
|---|---|---|
| *C08F 2/46* | (2006.01) | |
| *C08F 2/50* | (2006.01) | |
| *C08G 61/04* | (2006.01) | |
| *C08F 120/06* | (2006.01) | |
| *A61L 15/24* | (2006.01) | |
| *A61L 15/60* | (2006.01) | |
| *C08F 220/06* | (2006.01) | |

(52) U.S. Cl.
CPC ............ *C08F 120/06* (2013.01); *A61L 15/24* (2013.01); *A61L 15/60* (2013.01); *C08F 220/06* (2013.01)

(58) Field of Classification Search
CPC .......... C08J 3/075; C08J 2333/02; C08J 3/12; A61L 15/60; A61L 15/24; C08F 120/06; C08F 220/06; C08F 2222/1013
USPC ................ 522/64, 6, 71, 189, 184, 1; 520/1
See application file for complete search history.

(56) References Cited

U.S. PATENT DOCUMENTS

| | | | |
|---|---|---|---|
| 5,439,993 A | 8/1995 | Ito et al. | |
| 5,442,014 A | 8/1995 | Rebre et al. | |
| 6,174,929 B1 * | 1/2001 | Hahnle ................ | A61L 15/425 521/149 |
| 2010/0016522 A1 * | 1/2010 | Stueven ................ | C08F 6/008 526/60 |
| 2011/0136986 A1 | 6/2011 | Elliott et al. | |
| 2012/0035294 A1 * | 2/2012 | Kim ....................... | C08F 2/48 522/154 |
| 2013/0256593 A1 * | 10/2013 | Herfert ................ | B01J 20/267 252/194 |
| 2013/0324396 A1 * | 12/2013 | Honda .................. | C08F 6/006 502/402 |
| 2013/0338325 A1 * | 12/2013 | Peterson .............. | B01J 20/30 526/240 |
| 2014/0045683 A1 | 2/2014 | Loick et al. | |
| 2014/0053478 A1 * | 2/2014 | Peterson .............. | C08F 220/06 52/192 |
| 2015/0315321 A1 * | 11/2015 | Won ...................... | A61L 15/22 525/328.8 |
| 2016/0151531 A1 * | 6/2016 | Lee ....................... | B01J 20/267 525/328.9 |
| 2016/0184799 A1 * | 6/2016 | Lee ....................... | C08F 20/10 525/296 |
| 2016/0207026 A1 * | 7/2016 | Lee ....................... | C08J 3/245 |
| 2016/0280866 A1 * | 9/2016 | Lee ....................... | C08J 3/245 |
| 2016/0311985 A1 * | 10/2016 | Jung .................... | A61L 15/60 |
| 2016/0326286 A1 * | 11/2016 | Sim et al. ............. | C08F 220/06 |
| 2016/0332143 A1 * | 11/2016 | Sim et al. ............. | B01J 20/3085 |

FOREIGN PATENT DOCUMENTS

| | | |
|---|---|---|
| CN | 1067899 A | 1/1993 |
| EP | 0505163 A1 | 9/1992 |
| JP | 2902201 B2 | 6/1999 |
| JP | 2002105125 A | 4/2002 |
| JP | 2011530636 A | 12/2011 |
| KR | 19990057609 A | 7/1999 |
| KR | 20120013152 A | 2/2012 |
| KR | 10-1299649 B1 | 8/2013 |
| NO | 2008055856 A1 | 5/2008 |
| TW | 201217400 A | 5/2012 |
| WO | 2012132861 A1 | 10/2012 |
| WO | 2015-047029 * | 2/2015 |
| WO | 2015-047029 * | 4/2015 |

OTHER PUBLICATIONS

Search Report from International Application No. PCT/KR2015/005844, dated Sep. 22, 2015.
IPO Search Report from Tawian Application No. 104120169, dated Apr. 22, 2016.

* cited by examiner

*Primary Examiner* — Jessica E Whiteley
(74) *Attorney, Agent, or Firm* — Lerner, David, Littenberg, Krumholz & Mentlik, LLP

(57) ABSTRACT

Disclosed are a superabsorbent polymer including a water-soluble salt and a method of preparing the same, wherein the addition of a water-soluble metal salt in the polymerization process of a superabsorbent polymer is very effective at decreasing the concentration of residual monomer.

13 Claims, 3 Drawing Sheets

SUPER ABSORBENT POLYMER CONTAINING WATER-SOLUBLE SALT AND PREPARATION METHOD THEREFOR

CROSS-REFERENCE TO RELATED APPLICATION

The present application is a national phase entry under 35 U.S.C. §371 of International Application No. PCT/KR2015/005844, filed Jun. 10, 2015, which claims priority from Korean Application Nos. KR 10-2014-0076594, filed Jun. 23, 2014, and KR 10-2015-0081378, filed Jun. 9, 2015, all of which are incorporated herein by reference.

BACKGROUND OF THE INVENTION

1. Technical Field

The present invention relates to a superabsorbent polymer including a water-soluble salt and a method of preparing the same and, more particularly, to a superabsorbent polymer including a water-soluble salt and a method of preparing the same, wherein the addition of a water-soluble metal salt in the polymerization process of a superabsorbent polymer is very effective at decreasing the concentration of residual monomer (RM).

2. Description of the Related Art

Superabsorbent polymers (SAPs) are synthetic polymers able to absorb water about 500~1000 times their own weight. Such superabsorbent polymers have actually begun to be used for sanitary items, and are being currently widely utilized in not only hygiene products such as baby disposable diapers and so on, but also in gardening soil repair agents, water stop agents for civil construction, seeding sheets, freshness retaining agents in food distribution sectors, and fomentation materials. Compared to conventional absorbent materials, superabsorbent polymers have an outstanding absorption capacity and thus the market value thereof is increasing with the wider range of applications thereof.

The absorption mechanism of the superabsorbent polymer is controlled by osmotic pressure due to a difference in electric attraction represented by charges of a polymer electrolyte, an affinity between water and a polymer electrolyte, molecular expansion due to repulsive force between polymer electrolyte ions, and interactions of expansion inhibition due to crosslinkages. Briefly, absorbability of the absorbent polymer depends on the aforementioned affinity and molecular expansion, and the absorption rate thereof is greatly affected by osmotic pressure of the absorbent polymer itself.

In order to use the superabsorbent polymer as a hygiene material, the superabsorbent polymer has to essentially possess a low concentration of RM. To lower the concentration of RM, the use of acrylic acid having low dimer concentration is fundamentally adopted, and other methods may also be proposed but are problematic because other properties of the superabsorbent polymer may deteriorate or such additional processing may be complicated.

Therefore, thorough research is ongoing into preparation of superabsorbent polymers having high absorption rate and high absorption scale.

SUMMARY OF THE INVENTION

Accordingly, the present invention has been made keeping in mind the problems encountered in the related art, and an object of the present invention is to provide a superabsorbent polymer and a method of preparing the same, wherein adding a water-soluble metal salt is further included in a conventional method of preparing a superabsorbent polymer, thereby decreasing the concentration of RM.

In order to accomplish the above object, the present invention provides a method of preparing a superabsorbent polymer, comprising reacting a water-soluble ethylenic unsaturated monomer, a photoinitiator, a crosslinking agent, and a thermal polymerization initiator, in the presence of a water-soluble metal salt.

Furthermore, the method of preparing the superabsorbent polymer comprises: a) mixing the water-soluble ethylenic unsaturated monomer, the photoinitiator, and the crosslinking agent; b) diluting a sodium hydroxide aqueous solution with a water-soluble metal salt aqueous solution; c) neutralizing the mixture obtained in a) with the diluted solution obtained in b); d) adding the mixture obtained in c) with the thermal polymerization initiator, and then performing a radical polymerization reaction using thermal polymerization or photopolymerization, thus forming a polymer sheet; and e) adding the polymer sheet formed in d) with water, thus forming a hydrous gel polymer.

In addition, the present invention provides a superabsorbent polymer, prepared by the above method.

According to the present invention, a superabsorbent polymer is advantageous because the concentration of RM can be effectively lowered, compared to a conventional superabsorbent polymer.

DESCRIPTION OF THE SPECIFIC EMBODIMENTS

Figure 1:
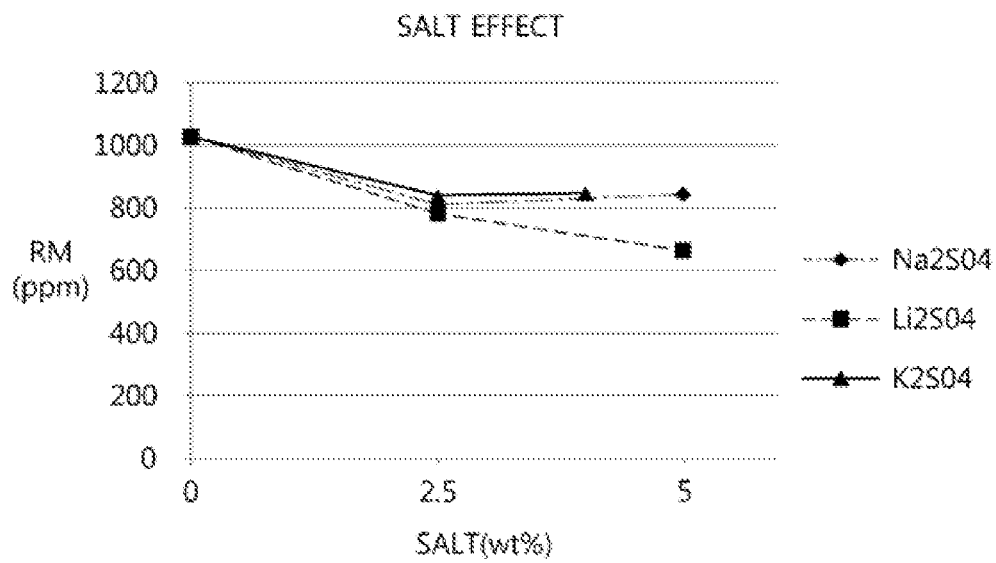
FIG. 1 is a graph illustrating changes in concentration of RM depending on the kind and amount of metal sulfate of a superabsorbent polymer according to an embodiment of the present invention.

Hereinafter, a detailed description will be given of the present invention.

The present invention addresses a method of preparing a superabsorbent polymer, comprising reacting a water-soluble ethylenic unsaturated monomer, a photoinitiator, a crosslinking agent, and a thermal polymerization initiator, in the presence of a water-soluble metal salt.

More specifically, the water-soluble metal salt preferably includes at least one selected from the group consisting of a sulfate group, a nitrate group, a phosphate group, a chloride group, a sulfite group, and a thiocyanate group. Particularly useful is a metal sulfate.

The metal of the water-soluble metal salt preferably includes at least one selected from the group consisting of sodium (Na), lithium (Li), potassium (K), aluminum (Al), zirconium (Zr), scandium (Sc), titanium (Ti), vanadium (V), chromium (Cr), manganese (Mn), iron (Fe), nickel (Ni), copper (Cu), zinc (Zn), silver (Ag), platinum (Pt), and gold (Au). Particularly useful is sodium (Na), lithium (Li), or potassium (K).

According to the present invention, the method of preparing the superabsorbent polymer comprises: a) mixing the water-soluble ethylenic unsaturated monomer, the photoinitiator, and the crosslinking agent; b) diluting a sodium hydroxide aqueous solution with a water-soluble metal salt aqueous solution; c) neutralizing the mixture obtained in a) with the diluted solution obtained in b); d) adding the mixture obtained in c) with the thermal polymerization initiator, and then performing a radical polymerization reaction using thermal polymerization or photopolymerization, thus forming a polymer sheet; and e) adding the polymer sheet formed in d) with water, thus forming a hydrous gel polymer.

The method may further comprise, after e) forming the hydrous gel polymer, f) drying and grinding the hydrous gel polymer, thus obtaining superabsorbent polymer particles; and g) sorting the superabsorbent polymer particles depending on the particle size, thus obtaining particles having a particle size of 150~850 μm.

As used herein, the term "superabsorbent polymer particles" refers to particles obtained by drying and grinding a hydrous gel polymer. More specifically, the hydrous gel polymer is a material in solid jelly form with a size of 1 cm or more having water in a large amount (50% or more) after completion of the polymerization. The hydrous gel polymer is dried and ground in a powder phase, yielding superabsorbent polymer particles. Thus, the hydrous gel polymer corresponds to a process intermediate.

In a) of the method of preparing the superabsorbent polymer according to the present invention, the water-soluble ethylenic unsaturated monomer, the photoinitiator and the crosslinking agent are mixed.

In the method of preparing the superabsorbent polymer according to the present invention, the water-soluble ethylenic unsaturated monomer is not particularly limited so long as it is a monomer typically used to synthesize a superabsorbent polymer, and preferably includes any one or more selected from the group consisting of an anionic monomer and salts thereof, a nonionic hydrophilic monomer, and an amino group-containing unsaturated monomer and quaternary salts thereof. Particularly useful is any one or more selected from the group consisting of anionic monomers and salts thereof, such as acrylic acid, methacrylic acid, maleic anhydride, fumaric acid, crotonic acid, itaconic acid, 2-acryloylethanesulfonic acid, 2-methacryloylethanesulfonic acid, 2-(meth)acryloylpropanesulfonic acid, and 2-(meth)acrylamide-2-methylpropane sulfonic acid; nonionic hydrophilic monomers, such as (meth)acrylamide, N-substituted (meth)acrylate, 2-hydroxyethyl(meth)acrylate, 2-hydroxypropyl (meth)acrylate, methoxypolyethyleneglycol (meth)acrylate, and polyethyleneglycol (meth)acrylate; and amino group-containing unsaturated monomers and quaternary salts thereof, such as (N,N)-dimethylaminoethyl (meth)acrylate, and (N,N)-dimethylaminopropyl (meth)acrylamide. More preferably, acrylic acid or salts thereof are used. When acrylic acid or salts thereof are used as the monomer, a superabsorbent polymer having improved absorbability may be obtained advantageously. Also, in the method of preparing the superabsorbent polymer according to the present invention, the concentration of the water-soluble ethylenic unsaturated monomer of the monomer composition may be appropriately determined in consideration of the polymerization time and the reaction conditions, and is preferably set to 40~55 wt %. If the concentration of the water-soluble ethylenic unsaturated monomer is less than 40 wt %, economic benefits are negated. In contrast, if the concentration thereof exceeds 55 wt %, grinding efficiency of the hydrous gel polymer may decrease.

In the method of preparing the superabsorbent polymer according to the present invention, the photoinitiator (photopolymerization initiator) is not particularly limited, but preferably includes at least one selected from the group consisting of benzoin ether, dialkyl acetophenone, hydroxyl alkylketone, phenyl glyoxylate, benzyl dimethyl ketal, acyl phosphine, and α-aminoketone. A specific example of the acyl phosphine may include commercially available lucirin TPO, namely, 2,4,6-trimethyl-benzoyl-trimethyl phosphine oxide, or commercially available Irgacure series may be used as the photoinitiator able to form a thick polymer layer with relatively high permeability.

In the method of preparing the superabsorbent polymer according to the present invention, the crosslinking agent is not limited so long as it is able to react with the functional group of the polymer. In order to improve the properties of the superabsorbent polymer, the crosslinking agent may include at least one selected from the group consisting of a polyhydric alcohol compound; an acrylate-based compound; an epoxy compound; a polyamine compound; a haloepoxy compound; a haloepoxy compound condensed product; an oxazoline compound; a mono-, di- or poly-oxazolidinone compound; a cyclic urea compound; a polyhydric metal salt; and an alkylene carbonate compound.

Specifically, the polyhydric alcohol compound may include at least one selected from the group consisting of mono-, di-, tri-, tetra- or poly-ethylene glycol, monopropylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, and 1,2-cyclohexanedimethanol.

The acrylate-based compound may be exemplified by poly(ethyleneglycol)diacrylate.

Examples of the epoxy compound may include ethylene glycol diglycidyl ether and glycidol, and the polyamine compound may include at least one selected from the group consisting of ethylene diamine, diethylene triamine, triethylene tetramine, tetraethylene pentamine, pentaethylene hexamine, polyethyleneimine, and polyamide polyamine.

Examples of the haloepoxy compound may include epichlorohydrine, epibromohydrine, and α-methylepichlorohydrine. The mono-, di- or poly-oxazolidinone compound may be exemplified by 2-oxazolidinone. The alkylene carbonate compound may include ethylene carbonate. These compounds may be used alone or in combination. To increase the efficiency of the crosslinking process, the crosslinking agent preferably includes at least one polyhydric alcohol compound, and more preferably includes a polyhydric alcohol compound having 2 to 10 carbon atoms.

The amount of the crosslinking agent added to treat the surface of the polymer particles may be properly determined depending on the kind of crosslinking agent or the reaction conditions, and is set to 0.001~5 parts by weight, preferably 0.01~3 parts by weight, and more preferably 0.05~2 parts by weight, based on 100 parts by weight of the polymer. If the amount of the crosslinking agent is too small, a crosslinking reaction seldom occurs. In contrast, if the amount thereof exceeds 5 parts by weight based on 100 parts by weight of the polymer, properties of the superabsorbent polymer may deteriorate due to an excessive crosslinking reaction.

In b), the alkaline aqueous solution is diluted with the water-soluble metal salt aqueous solution.

The alkaline aqueous solution is preferably a sodium hydroxide (NaOH) aqueous solution or a potassium hydroxide (KOH) aqueous solution. More preferably useful is a sodium hydroxide (NaOH) aqueous solution.

The water-soluble metal salt preferably includes at least one selected from the group consisting of a sulfate group, a nitrate group, a phosphate group, a chloride group, a sulfite group, and a thiocyanate group. Particularly useful is a metal sulfate.

The metal of the water-soluble metal salt preferably includes at least one selected from the group consisting of sodium (Na), lithium (Li), potassium (K), aluminum (Al), zirconium (Zr), scandium (Sc), titanium (Ti), vanadium (V), chromium (Cr), manganese (Mn), iron (Fe), nickel (Ni), copper (Cu), zinc (Zn), silver (Ag), platinum (Pt), and gold (Au). Particularly useful is sodium (Na), lithium (Li), or potassium (K).

The water-soluble metal salt is preferably used in an amount of 0.001~40.0 wt %, more preferably 2.0~20.0 wt %, and still more preferably 2.5~15.0 wt %, based on the total weight of the water-soluble ethylenic unsaturated monomer. If the amount of the water-soluble metal salt is less than 0.001 wt %, an effect of decreasing the concentration of RM may become insignificant. In contrast, if the amount thereof exceeds 40.0 wt %, the main component of the superabsorbent polymer may be undesirably changed into a salt, but not the monomer. Taking into consideration the mixing ratio of components, the maximum amount of the above component is determined.

The water-soluble metal salt does not directly participate in an actual chemical reaction and has an electrostatic influence on cation transfer. The water-soluble ethylenic unsaturated monomer is mixed with a sodium hydroxide aqueous solution so as to be partially neutralized, followed by radical polymerization. As such, the water-soluble metal salt may be added to decrease electrical repulsion between anionic monomers. The cation of the water-soluble metal salt is regarded as important, and the repulsion between monomers may be decreased by virtue of a shielding effect due to the cation, thus enabling efficient polymerization. Consequently, the superabsorbent polymer prepared by the above method may be expected to exhibit an effect of decreasing the concentration of RM.

In c), the mixture obtained in a) is introduced with the diluted solution obtained in b) so as to be neutralized. As such, c) may be carried out at 30~50° C.

In d), the mixture obtained in c) is further added with the thermal polymerization initiator, after which radical polymerization using thermal polymerization or photopolymerization may be implemented, thus forming a polymer sheet.

The superabsorbent polymer according to the present invention may be prepared by steps and methods typically used in the art. Specifically, upon preparation of the superabsorbent polymer according to the present invention, the monomer composition includes a polymerization initiator. Depending on the polymerization method, when photopolymerization is performed, a photopolymerization initiator is used, and when thermal polymerization is performed, a thermal polymerization initiator is employed. Even when the photopolymerization is conducted, a predetermined amount of heat is generated due to irradiation with UV light and also through the polymerization, which is an exothermic reaction, and thus a thermal polymerization initiator may be additionally used.

In the method of preparing the superabsorbent polymer according to the present invention, the thermal polymerization initiator is not particularly limited, but preferably includes at least one selected from the group consisting of a persulfate-based initiator, an azo-based initiator, hydrogen peroxide, and ascorbic acid. Specifically, examples of the persulfate-based initiator may include sodium persulfate ($Na_2S_2O_8$), potassium persulfate ($K_2S_2O_8$), and ammonium persulfate (($NH_4)_2S_2O_8$); and examples of the azo-based initiator may include 2,2-azobis(2-amidinopropane)dihydrochloride, 2,2-azobis-(N,N-dimethylene)isobutyramidine dihydrochloride, 2-(carbamoylazo)isobutyronitrile, 2,2-azobis-[2-(2-imidazolin-2-yl)propane]dihydrochloride, and 4,4-azobis-(4-cyanovaleric acid).

Also, the polymerization method is largely classified into thermal polymerization and photopolymerization depending on the polymerization energy source. Typically, thermal polymerization is conducted using a reactor with a stirring shaft, such as a kneader, and photopolymerization is implemented using a reactor with a movable conveyor belt. However, the above polymerization method is merely illustrative, and the present invention is not limited to such a polymerization method.

For example, hot air is fed to a reactor with a stirring shaft, such as a kneader, or the reactor is heated, so that thermal polymerization is carried out, yielding a hydrous gel polymer, which is then discharged to a size ranging from ones of mm to ones of cm through the outlet of the reactor depending on the shape of the stirring shaft of the reactor. Specifically, the size of the hydrous gel polymer may vary depending on the concentration of the supplied monomer composition and the supply rate thereof, and typically a hydrous gel polymer having a particle size of 2~50 mm may be obtained.

Also, when photopolymerization is carried out using a reactor with a movable conveyor belt, a hydrous gel polymer in a sheet form with a belt width may result. As such, the thickness of the polymer sheet may vary depending on the concentration of the supplied monomer composition and the supply rate thereof, but the monomer composition is preferably supplied so as to obtain a polymer sheet having a thickness of 0.5~5 cm. In the case where the monomer composition is supplied to the extent that a very thin polymer sheet is formed, production efficiency may decrease undesirably. If the thickness of the polymer sheet is greater than 5 cm, polymerization may not be uniformly carried out throughout the sheet that is too thick.

In an embodiment of the present invention, thermal polymerization or photopolymerization in d) may be implemented by applying at least one heat source selected from the group consisting of steam, electricity, UV light, and IR light. As such, UV light may be applied at an intensity 1~20 mW/cm$^2$.

In e), the polymer sheet formed in d) is added with water, yielding a hydrous gel polymer.

The hydrous gel polymer thus obtained typically has a moisture content of 30~60 wt %. As used herein, the term "moisture content" refers to an amount of moisture based on the total weight of the hydrous gel polymer, namely, a value obtained by subtracting the weight of the dried polymer from the weight of the hydrous gel polymer (Specifically, it is defined as a value calculated by measuring a weight reduction due to moisture evaporation from the polymer during drying the polymer at high temperature via IR heating. As such, the drying is performed in such a manner that the temperature is increased from room temperature to 180° C. and then maintained at 180° C., and the total drying time is set to 20 min including 5 min necessary for increasing the temperature).

In f), the hydrous gel polymer is dried and ground, thus obtaining superabsorbent polymer particles.

In the drying process, the drying temperature may be set to 150~250° C. As used herein, the term "drying temperature" refers to a temperature of a heat medium supplied for the drying process or a temperature of a drying reactor including a heat medium and a polymer in the drying process.

If the drying temperature is lower than 150° C., the drying time may become excessively long, and the properties of the final superabsorbent polymer may thus deteriorate. In contrast, if the drying temperature is higher than 250° C., only the surface of the polymer may be excessively dried, and thereby fine powder may be generated in the subsequent grinding process, and the properties of the final superabsorbent polymer may deteriorate. The drying is preferably performed at a temperature of 150~250° C., and more preferably 160~200° C.

The drying time is not limited, but may be set to 20~90 min taking into account the process efficiency.

Also, the drying process is not limited so long as it is typically used to dry the hydrous gel polymer. Specific examples thereof may include hot air supply, IR irradiation, microwave irradiation, and UV irradiation. The polymer after the drying process may have a moisture content of 0.1~10 wt %.

Meanwhile, the method of preparing the superabsorbent polymer according to the present invention may further comprise a simple grinding process before the drying process, as necessary, in order to increase the drying efficiency. The simple grinding process before the drying process is conducted so that the particle size of the hydrous gel polymer is 1~15 mm. Grinding the particle size of the polymer to less than 1 mm is technically difficult due to high moisture content of the hydrous gel polymer, and also the ground particles may agglomerate. In contrast, if the polymer is ground to a particle size of greater than 15 mm, an effect of increasing the drying efficiency via the grinding process may become insignificant.

In the simple grinding process before the drying process, any grinder may be used without limitation. A specific example thereof may include, but is not limited to, any one selected from the group consisting of a vertical pulverizer, a turbo cutter, a turbo grinder, a rotary cutter mill, a cutter mill, a disc mill, a shred crusher, a crusher, a chopper, and a disc cutter.

When the grinding process is performed to increase the drying efficiency before the drying process in this way, the polymer having high moisture content may stick to the surface of the grinder. Thus, in order to increase the grinding efficiency of the hydrous gel polymer before the drying process, an additive able to prevent stickiness upon grinding may be further used. Specifically, the kind of usable additive is not limited. Examples thereof may include, but are not limited to, a powder agglomeration inhibitor, such as steam, water, a surfactant, and inorganic powder such as clay or silica; a thermal polymerization initiator, such as a persulfate-based initiator, an azo-based initiator, hydrogen peroxide, and ascorbic acid; and a crosslinking agent, such as an epoxy-based crosslinking agent, a diol-based crosslinking agent, a bifunctional or trifunctional or higher polyfunctional acrylate, and a monofunctional compound having a hydroxyl group.

In g), the superabsorbent polymer particles are sorted depending on the particle size, thus obtaining particles having a particle size of 150~850 μm.

The superabsorbent polymer particles resulting from the grinding process have a particle size of 150~850 μm. In the method of preparing the superabsorbent polymer according to the present invention, a grinder used to obtain such a particle size may include, but is not limited to, a pin mill, a hammer mill, a screw mill, a roll mill, a disc mill, or a jog mill.

In addition, the present invention addresses a superabsorbent polymer prepared by the preparation method as above. As measured by an EDANA measurement method, such a superabsorbent polymer is advantageous because the concentration of RM is lowered by the addition of the water-soluble metal salt, compared to when the water-soluble metal salt is not added.

A better understanding of the present invention may be obtained via the following examples that are set forth to illustrate, but are not to be construed as limiting the scope of the present invention. The scope of the present invention is shown in the claims, and also contains all modifications within the meaning and range equivalent to the claims. Unless otherwise mentioned, "%" and "part" showing the amount in the following examples and comparative examples refer to a mass basis.

Examples 1 to 7 and Comparative Example 1: Preparation of Superabsorbent Polymer Example 1

192.7 g of an aqueous solution having 13.0 g (2.5 wt % based on acrylic acid) of $Na_2SO_4$ dissolved therein was used to dilute 629.6 g of a 32 wt % sodium hydroxide aqueous solution, after which acrylic acid, Irgacure 819 as a photoinitiator, and PEGDA (Poly(ethyleneglycol)diacrylate) as a crosslinking agent were sequentially added using a pump. The resulting mixture was gradually cooled using a cooler, placed in a plastic beaker containing a sodium persulfate aqueous solution as a thermal initiator, poured into a pre-stabilized UV irradiator, and then irradiated with UV light (at an intensity of 10 mW/cm$^2$). The point of time when a foaming sound was heard was measured using a stopwatch, and UV irradiation was stopped when the measurement time reached 1 min, and the resulting product was allowed to stand for 2 min in the UV irradiator. The polymerized sheet was snipped, uniformly mixed with 250 g of water so as to absorb such water, and then cut into small pieces using a chopper. The small pieces thus cut were evenly spread in an oven, dried and then ground. Then, a superabsorbent polymer having a particle size of 150~850 μm was obtained using a standard sieve.

Example 2

In 192.7 g of water used to dilute sodium hydroxide in Example 1, 25.9 g (5.0 wt % based on acrylic acid) of $Na_2SO_4$ was dissolved, after which the same procedures as in Example 1 were performed, yielding a superabsorbent polymer.

Example 3

In 192.7 g of water used to dilute sodium hydroxide in Example 1, 77.7 g (15.0 wt % based on acrylic acid) of $Na_2SO_4$ was dissolved, after which the same procedures as in Example 1 were performed, yielding a superabsorbent polymer.

Example 4

In 192.7 g of water used to dilute sodium hydroxide in Example 1, 13.0 g (2.5 wt % based on acrylic acid) of Li$_2$SO$_4$ was dissolved, after which the same procedures as in Example 1 were performed, yielding a superabsorbent polymer.

Example 5

In 192.7 g of water used to dilute sodium hydroxide in Example 1, 25.9 g (5.0 wt % based on acrylic acid) of Li$_2$SO$_4$ was dissolved, after which the same procedures as in Example 1 were performed, yielding a superabsorbent polymer.

Example 6

In 192.7 g of water used to dilute sodium hydroxide in Example 1, 13.0 g (2.5 wt % based on acrylic acid) of K$_2$SO$_4$ was dissolved, after which the same procedures as in Example 1 were performed, yielding a superabsorbent polymer.

Example 7

In 192.7 g of water used to dilute sodium hydroxide in Example 1, 20.7 g (4.0 wt % based on acrylic acid) of K$_2$SO$_4$ was dissolved, after which the same procedures as in Example 1 were performed, yielding a superabsorbent polymer.

Comparative Example 1

A superabsorbent polymer was prepared in the same manner as in Example 1, with the exception that the water-soluble metal salt was not added.

The amounts of salts in Examples 1 to 7 and Comparative Example 1 are given in Table 1 below.

TABLE 1

| | | Amount of Salt | |
|---|---|---|---|
| | Salt | wt % based on acrylic acid | Weight (g) |
| Ex. 1 | Na$_2$SO$_4$ | 2.5 | 13.0 |
| Ex. 2 | | 5.0 | 25.9 |
| Ex. 3 | | 15.0 | 77.7 |
| Ex. 4 | Li$_2$SO$_4$ | 2.5 | 13.0 |
| Ex. 5 | | 5.0 | 25.9 |
| Ex. 6 | K$_2$SO$_4$ | 2.5 | 13.0 |
| Ex. 7 | | 4.0 | 20.7 |
| C. Ex. 1 | None | — | — |

Test Example: Evaluation of Properties of Superabsorbent Polymer

To evaluate the properties of the superabsorbent polymers of Examples 1 to 7 and Comparative Example 1, the following testing was performed.

Residual Monomer (RM)

In the superabsorbent polymers of Examples 1 to 7 and Comparative Example 1, the concentration of RM was measured based on WSP 210.3 according to an EDANA method. 1.000 g of a superabsorbent polymer sample having a particle size of 150~850 μm and 200 g of 0.9% brine were placed in a 250 mL Erlenmeyer flask and stirred for 1 hr. Subsequently, the resulting mixture was filtered using filter paper, and the solution was sampled and measured by HPLC.

Also, in the superabsorbent polymers of the examples and comparative example, changes in the concentration of RM depending on the kind and amount of metal sulfate were measured. The results are shown in Table 2 below and FIG. 1.

TABLE 2

| | Metal sulfate | | |
|---|---|---|---|
| | Kind | wt % | RM (ppm) |
| Ex. 1 | Na$_2$SO$_4$ | 2.5 | 804 |
| Ex. 2 | | 5.0 | 850 |
| Ex. 3 | | 15.0 | 822 |
| Ex. 4 | Li$_2$SO$_4$ | 2.5 | 794 |
| Ex. 5 | | 5.0 | 676 |
| Ex. 6 | K$_2$SO$_4$ | 2.5 | 848 |
| Ex. 7 | | 4.0 | 853 |
| C. Ex. 1 | — | — | 977 |

The concentration values of RM in the above examples and comparative example are average values of several tests.

As is apparent from Table 2 and FIG. 1, when the water-soluble metal salt, that is, the metal sulfate, was added in the polymerization process of a superabsorbent polymer, the concentration of RM was effectively decreased, compared to when the metal sulfate was not added (Comparative Example 1).

Figure 2A:
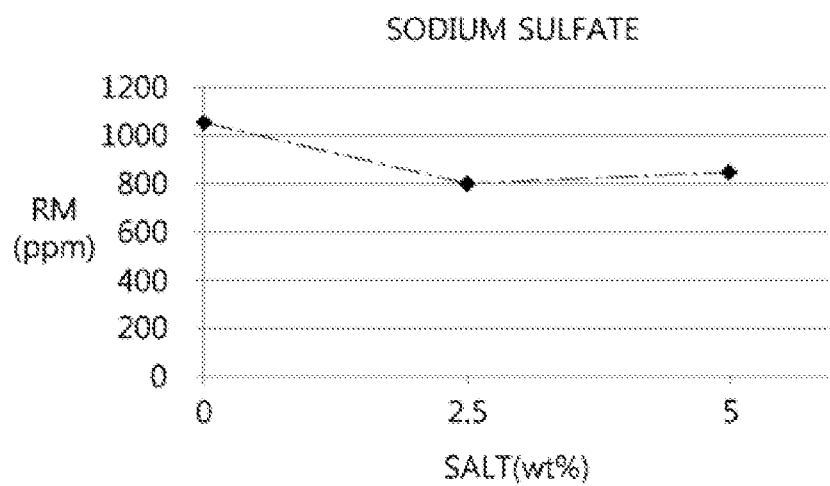
FIGS. 2A to 2C are graphs illustrating changes in concentration of RM depending on the kind and amount of metal sulfate.
Figure 2B:
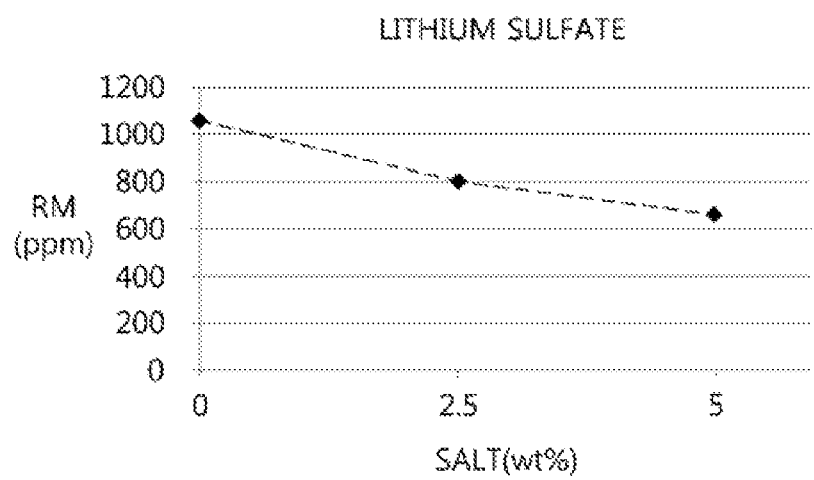
Figure 2C:
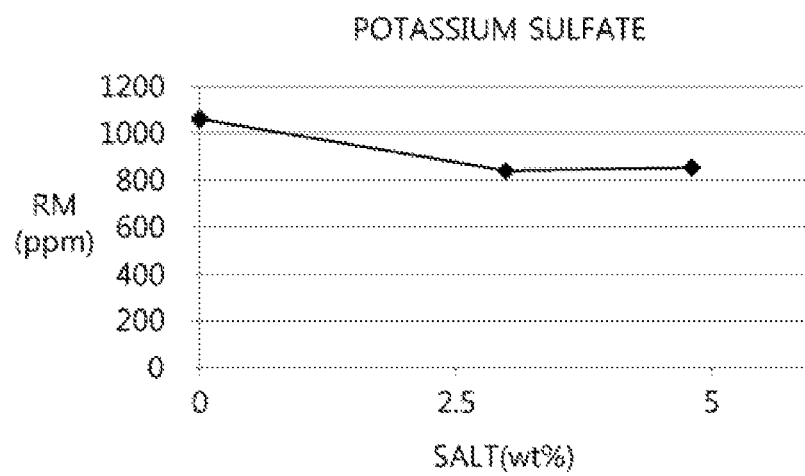

More specifically, FIGS. 2A to 2C are graphs illustrating changes in the concentration of RM depending on the kind and amount of metal sulfate. Based on the average concentration values of RM, when the water-soluble metal salt, that is, the metal sulfate was added in the same amount (mass) depending on the kind thereof, the salts effective at decreasing the concentration of RM were represented by the sequence of Li$_2$SO$_4$>Na$_2$SO$_4$>K$_2$SO$_4$, or were represented by the sequence of Li$_2$SO$_4$>K$_2$SO$_4$>Na$_2$SO$_4$ in some cases. Although the extent of decrease in concentration of RM varied depending on the amount of the salt, there were significant differences in the effects due to the presence or absence of the metal sulfate as the water-soluble metal salt.

Figure 3:
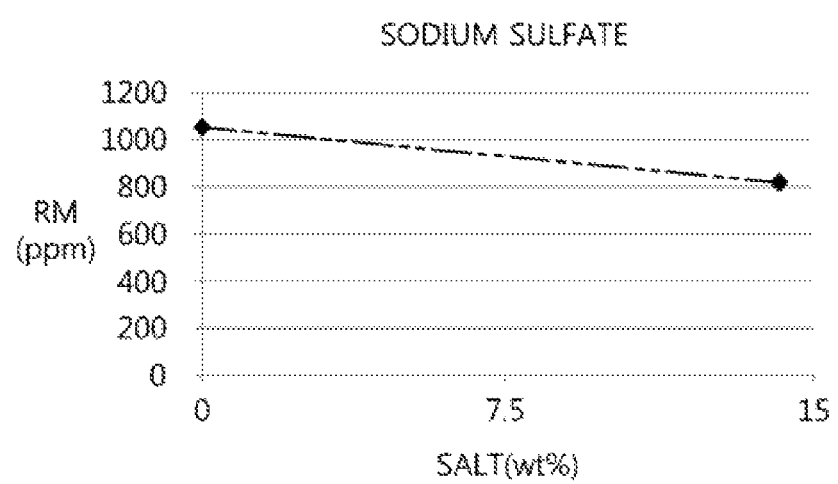
FIG. 3 is a graph illustrating a decrease in concentration of RM when $Na_2SO_4$ as a metal sulfate is added in an excessive amount (15 wt %).

As illustrated in FIG. 3, when the water-soluble metal salt, that is, the metal sulfate Na$_2$SO$_4$ was added in an excessive amount (15 wt %), the concentration of RM was uniformly decreased in a negative (−) slope, compared to when the metal sulfate was not added (Comparative Example 1). Thereby, the effect of the metal sulfate on decreasing the concentration of RM was superior despite the excessive use thereof.

Therefore, the superabsorbent polymer according to the present invention can be effectively decreased in the concentration of RM by the addition of a water-soluble metal salt, compared to a conventional superabsorbent polymer.

What is claimed is:

1. A method of preparing a superabsorbent polymer, comprising reacting a water-soluble ethylenic unsaturated monomer, a photoinitiator, a crosslinking agent, and a thermal polymerization initiator, in the presence of a water-soluble metal salt,
wherein the water-soluble metal salt comprises a sulfate group.

2. The method of claim 1, wherein a metal of the water-soluble metal salt comprises at least one selected from the group consisting of sodium (Na), lithium (Li), potassium (K), aluminum (Al), zirconium (Zr), scandium (Sc), titanium (Ti), vanadium (V), chromium (Cr), manganese (Mn), iron (Fe), nickel (Ni), copper (Cu), zinc (Zn), silver (Ag), platinum (Pt), and gold (Au).

3. The method of claim 1, wherein the water-soluble metal salt is contained in an amount of 0.001~40.0 wt %, based on a total weight of the water-soluble ethylenic unsaturated monomer.

4. The method of claim 1, comprising:
a) mixing the water-soluble ethylenic unsaturated monomer, the photoinitiator, and the crosslinking agent;
b) diluting an alkaline aqueous solution with a water-soluble metal salt aqueous solution;
c) neutralizing a mixture obtained in a) with a diluted solution obtained in b);
d) adding a mixture obtained in c) with the thermal polymerization initiator, and then performing a radical polymerization reaction using thermal polymerization or photopolymerization, thus forming a polymer sheet; and
e) adding the polymer sheet formed in d) with water, thus forming a hydrous gel polymer.

5. The method of claim 4, further comprising, after e) forming the hydrous gel polymer,
f) drying and grinding the hydrous gel polymer, thus obtaining superabsorbent polymer particles; and
g) sorting the superabsorbent polymer particles depending on a particle size, thus obtaining particles having a particle size of 150~850 μm.

6. The method of claim 4, wherein the alkaline aqueous solution is a sodium hydroxide (NaOH) aqueous solution or a potassium hydroxide (KOH) aqueous solution.

7. The method of claim 1, wherein the water-soluble ethylenic unsaturated monomer comprises at least one selected from the group consisting of an anionic monomer and salts thereof, including acrylic acid, methacrylic acid, maleic anhydride, fumaric acid, crotonic acid, itaconic acid, 2-acryloylethanesulfonic acid, 2-methacryloylethanesulfonic acid, 2-(meth)acryloylpropanesulfonic acid, and 2-(meth)acrylamide-2-methylpropane sulfonic acid; a nonionic hydrophilic monomer, including (meth)acrylamide, N-substituted (meth)acrylate, 2-hydroxyethyl(meth)acrylate, 2-hydroxypropyl(meth)acrylate, methoxypolyethyleneglycol (meth)acrylate, and polyethyleneglycol (meth)acrylate; and an amino group-containing unsaturated monomer and quaternary salts thereof, including (N,N)-dimethylaminoethyl (meth)acrylate, and (N,N)-dimethylaminopropyl (meth)acrylamide.

8. The method of claim 1, wherein the photoinitiator comprises at least one selected from the group consisting of benzoin ether, dialkyl acetophenone, hydroxyl alkylketone, phenyl glyoxylate, benzyl dimethyl ketal, acyl phosphine, and α-aminoketone.

9. The method of claim 1, wherein the crosslinking agent comprises at least one selected from the group consisting of a polyhydric alcohol compound; an acrylate-based compound; an epoxy compound; a polyamine compound; a haloepoxy compound; a haloepoxy compound condensed product; an oxazoline compound; a mono-, di- or poly-oxazolidinone compound; a cyclic urea compound; a polyhydric metal salt; and an alkylene carbonate compound.

10. The method of claim 4, wherein c) is performed at 30~50° C.

11. The method of claim 1, wherein the thermal polymerization initiator comprises at least one selected from the group consisting of a persulfate-based initiator, including sodium persulfate ($Na_2S_2O_8$), potassium persulfate ($K_2S_2O_8$), and ammonium persulfate (($NH_4)_2S_2O_8$); an azo-based initiator, including 2,2-azobis(2-amidinopropane)dihydrochloride, 2,2-azobis-(N,N-dimethylene)isobutyramidine dihydrochloride, 2-(carbamoylazo)isobutyronitrile, 2,2-azobis [2-(2-imidazolin-2-yl)propane]dihydrochloride, and 4,4-azobis-(4-cyanovaleric acid); hydrogen peroxide; and ascorbic acid.

12. The method of claim 4, wherein the thermal polymerization or photopolymerization in d) is performed by irradiation with at least one heat source selected from the group consisting of steam, electricity, UV light, and IR light.

13. The method of claim 12, wherein the irradiation with UV light is performed by applying UV light at an intensity of 1~20 mW/cm$^2$.

* * * * *